(12) United States Patent
Werneth

(10) Patent No.: US 6,719,723 B2
(45) Date of Patent: Apr. 13, 2004

(54) MULTIPURPOSE CATHETER ASSEMBLY

(75) Inventor: Randell Werneth, Poway, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 09/731,176

(22) Filed: Dec. 6, 2000

(65) Prior Publication Data

US 2002/0068901 A1 Jun. 6, 2002

(51) Int. Cl.$^7$ ................................................. A61F 7/12
(52) U.S. Cl. ....................................................... 604/113
(58) Field of Search .............................. 604/113, 4, 5, 604/6; 607/96, 104, 105, 106, 113, 114

(56) References Cited

U.S. PATENT DOCUMENTS

| 2,672,032 A | 3/1954 | Towse |
| 2,913,009 A | 11/1959 | Kuthe et al. |
| 3,125,096 A | 3/1964 | Antiles et al. |
| 3,425,419 A | 2/1969 | Dato |
| 3,604,419 A | 9/1971 | Diskin et al. |
| 3,612,175 A | 10/1971 | Ford et al. |
| 4,038,519 A | 7/1977 | Foucras |
| 4,160,455 A | 7/1979 | Law |
| 4,190,033 A | 2/1980 | Foti |
| 4,298,006 A | 11/1981 | Parks |

(List continued on next page.)

FOREIGN PATENT DOCUMENTS

| AU | 730835 B2 | 3/2001 |
| AU | 734506 B2 | 6/2001 |
| AU | 739996 B2 | 2/2002 |
| AU | 743945 B2 | 2/2002 |
| EP | 1205167 A2 | 5/2002 |
| EP | 1029520 B1 | 8/2002 |
| WO | WO91/05528 | 5/1991 |
| WO | WO 96/40347 | 5/1996 |
| WO | WO97/25011 A1 | 7/1997 |
| WO | WO 98/26831 | 6/1998 |
| WO | WO98/26831 A1 | 6/1998 |
| WO | WO98/31312 A1 | 7/1998 |
| WO | WO99/37226 A1 | 7/1999 |
| WO | WO99/48449 A1 | 9/1999 |
| WO | WO99/66970 A1 | 12/1999 |
| WO | WO99/66971 A1 | 12/1999 |
| WO | WO00/09054 A1 | 2/2000 |
| WO | WO00/10494 A1 | 3/2000 |

(List continued on next page.)

OTHER PUBLICATIONS

Colvett, K. Opportunities with combined modality therapy for selective organ preservation in muscle–invasive bladder cancer. *Journal of surgical oncology, vol. 63, No. 3,* pp. 201–208, 1996.
Maas, C. Intermittent antegrade selective cerebral perfusion during circulatory arrest for repair of aortic arch. *Perfusion, vol. 12, No. 2,* pp. 127–132, 1997.

*Primary Examiner*—Henry Bennett
*Assistant Examiner*—Sabrina Dagostino
(74) *Attorney, Agent, or Firm*—Gerald W. Spinks

(57) ABSTRACT

An apparatus for performing hypothermia of the body of a patient, or of a selected organ, while delivering a medicament to a selected blood vessel. A flexible coaxial catheter is inserted through the vascular system of a patient to place the distal tip of the catheter in a selected artery. A chilled fluid is pumped through an inner supply conduit of the catheter to cool a flexible heat transfer element in the distal tip of the catheter. The heat transfer element cools the blood flowing through the artery distal to the tip of the catheter. The medicament, such as a vaso-dilator, is delivered either separately or mixed with the chilled fluid, through a very small exit port in or near the heat transfer element.

24 Claims, 2 Drawing Sheets

U.S. PATENT DOCUMENTS

| | | |
|---|---|---|
| 4,323,071 A | 4/1982 | Simpson et al. |
| 4,464,172 A | 8/1984 | Lichtenstein |
| 4,602,642 A | 7/1986 | O'Hara et al. |
| 4,745,922 A | 5/1988 | Taylor |
| 4,747,826 A | 5/1988 | Sassano |
| 4,781,799 A | 11/1988 | Herbert, Jr. et al. |
| 4,871,351 A | 10/1989 | Feingold |
| 4,951,677 A | 8/1990 | Crowley et al. |
| 4,969,470 A | 11/1990 | Mohl et al. |
| 4,979,959 A | 12/1990 | Guire |
| 5,000,734 A | 3/1991 | Boussignac et al. |
| 5,024,668 A | 6/1991 | Peters et al. |
| 5,046,497 A | 9/1991 | Millar |
| 5,089,260 A | 2/1992 | Hunter et al. |
| 5,106,368 A | 4/1992 | Uldall et al. |
| 5,112,438 A | 5/1992 | Bowers |
| 5,150,706 A | 9/1992 | Cox et al. |
| 5,180,364 A | 1/1993 | Ginsburg |
| 5,190,539 A | 3/1993 | Fletcher et al. |
| 5,211,631 A | 5/1993 | Sheaff |
| 5,236,908 A | 8/1993 | Gruber et al. |
| 5,257,977 A | 11/1993 | Eshel |
| 5,267,341 A | 11/1993 | Shearin |
| 5,269,758 A | 12/1993 | Taheri |
| 5,306,261 A | 4/1994 | Alliger et al. |
| 5,320,503 A | 6/1994 | Davis |
| 5,322,514 A | 6/1994 | Steube et al. |
| 5,322,515 A | 6/1994 | Karas et al. |
| 5,322,518 A | 6/1994 | Schneider et al. |
| 5,324,319 A | 6/1994 | Mason et al. |
| 5,326,236 A | 7/1994 | Kramer et al. |
| 5,328,461 A | 7/1994 | Utterberg |
| 5,330,435 A | 7/1994 | Vaillancourt |
| 5,330,438 A | 7/1994 | Gollobin et al. |
| 5,331,309 A | 7/1994 | Sakai |
| 5,334,179 A | 8/1994 | Poli et al. |
| 5,334,180 A | 8/1994 | Adolf et al. |
| 5,334,188 A | 8/1994 | Inoue et al. |
| 5,334,197 A | 8/1994 | Kriesel et al. |
| 5,336,190 A | 8/1994 | Moss et al. |
| 5,339,511 A | 8/1994 | Bell |
| 5,342,347 A | 8/1994 | Kikuchi et al. |
| 5,343,734 A | 9/1994 | Maeda et al. |
| 5,346,466 A | 9/1994 | Yerlikaya et al. |
| 5,352,213 A | 10/1994 | Woodard |
| 5,354,264 A | 10/1994 | Bae et al. |
| 5,354,272 A | 10/1994 | Swendson et al. |
| 5,364,364 A | 11/1994 | Kasvikis et al. |
| 5,383,854 A | 1/1995 | Safar et al. |
| 5,395,331 A | 3/1995 | O'Neill et al. |
| 5,423,807 A | 6/1995 | Milder |
| 5,437,673 A | 8/1995 | Baust et al. |
| 5,486,208 A | 1/1996 | Ginsburg |
| 5,496,271 A | 3/1996 | Burton et al. |
| 5,520,682 A | 5/1996 | Baust et al. |
| 5,531,776 A | 7/1996 | Ward et al. |
| 5,536,247 A | 7/1996 | Thornton |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,622,182 A | 4/1997 | Jaffe |
| 5,624,392 A | 4/1997 | Saab |
| 5,630,837 A | 5/1997 | Crowley |
| 5,643,197 A | 7/1997 | Brucker et al. |
| 5,653,692 A | 8/1997 | Masterson et al. |
| 5,709,654 A | 1/1998 | Klatz et al. |
| 5,733,318 A | 3/1998 | Augustine |
| 5,733,319 A | 3/1998 | Neilson et al. |
| 5,735,809 A | 4/1998 | Gorsuch |
| 5,799,661 A | 9/1998 | Boyd et al. |
| 5,800,483 A | 9/1998 | Vought |
| 5,800,488 A | 9/1998 | Crocket |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |
| 5,827,269 A | 10/1998 | Saadat |
| 5,833,673 A | 11/1998 | Ockuly et al. |
| 5,834,465 A | 11/1998 | Olney |
| 5,837,003 A | 11/1998 | Ginsburg |
| 5,861,021 A | 1/1999 | Thome et al. |
| 5,868,735 A | 2/1999 | Lafontaine |
| 5,873,835 A | 2/1999 | Hastings et al. |
| 5,879,316 A | 3/1999 | Safar et al. |
| 5,879,329 A | 3/1999 | Ginsburg |
| 5,899,898 A | 5/1999 | Arless et al. |
| 5,899,899 A | 5/1999 | Arless et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,957,917 A | 9/1999 | Doiron et al. |
| 5,957,963 A | 9/1999 | Dobak, III |
| 5,964,751 A | 10/1999 | Amplatz et al. |
| 5,967,976 A | 10/1999 | Larsen et al. |
| 5,968,009 A | 10/1999 | Simán |
| 5,971,979 A | 10/1999 | Joye et al. |
| 5,989,238 A | 11/1999 | Ginsburg |
| 6,007,692 A | 12/1999 | Herbert et al. |
| 6,011,995 A | 1/2000 | Guglielmi et al. |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,042,559 A | 3/2000 | Dobak, III |
| 6,051,019 A | 4/2000 | Dobak, III |
| 6,063,101 A | 5/2000 | Jacobsen et al. |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,156,007 A * | 12/2000 | Ash .......................... 604/113 |
| 6,165,207 A | 12/2000 | Balding et al. |
| 6,182,666 B1 | 2/2001 | Dobak, III |
| 6,206,004 B1 | 3/2001 | Schmidt et al. |
| 6,224,624 B1 | 5/2001 | Lasheras et al. |
| 6,231,594 B1 | 5/2001 | Dae |
| 6,231,595 B1 | 5/2001 | Dobak, III |
| 6,235,048 B1 | 5/2001 | Dobak, III |
| 6,238,428 B1 | 5/2001 | Werneth et al. |
| 6,245,095 B1 | 6/2001 | Dobak, III et al. |
| 6,248,057 B1 | 6/2001 | Mavity et al. |
| 6,251,129 B1 | 6/2001 | Dobak, III et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,270,494 B1 | 8/2001 | Kovalcheck et al. |
| 6,287,326 B1 | 9/2001 | Pecor |
| 6,290,697 B1 | 9/2001 | Tu et al. |
| 6,290,717 B1 | 9/2001 | Philips |

| | | |
|---|---|---|
| 6,295,990 B1 | 10/2001 | Lewis et al. |
| 6,299,599 B1 | 10/2001 | Pham et al. |
| 6,306,161 B1 | 10/2001 | Ginsburg |
| 6,312,452 B1 | 11/2001 | Dobak, III et al. |
| 6,325,818 B1 | 12/2001 | Werneth |
| 6,338,727 B1 | 1/2002 | Noda et al. |
| 6,364,899 B1 | 4/2002 | Dobak, III |
| 6,368,304 B1 | 4/2002 | Aliberto et al. |
| 6,379,378 B1 | 4/2002 | Werneth et al. |
| 6,383,210 B1 | 5/2002 | Magers et al. |
| 6,393,320 B2 | 5/2002 | Lasersohn et al. |
| 6,405,080 B1 | 6/2002 | Lasersohn et al. |
| 6,409,747 B1 | 6/2002 | Gobin et al. |
| 6,416,533 B1 | 7/2002 | Gobin et al. |
| 6,419,643 B1 | 7/2002 | Shimada t al. |
| 6,428,563 B1 | 8/2002 | Keller |
| 6,432,124 B1 | 8/2002 | Worthen et al. |
| 6,436,130 B1 | 8/2002 | Philips et al. |
| 6,436,131 B1 | 8/2002 | Ginsburg |
| 6,447,474 B1 | 9/2002 | Balding |
| 6,450,990 B1 | 9/2002 | Walker et al. |
| 6,454,792 B1 | 9/2002 | Noda et al. |
| 6,454,793 B1 | 9/2002 | Evans et al. |
| 6,458,150 B1 | 10/2002 | Evans et al. |
| 2001/0001064 A1 | 5/2001 | Holaday |
| 2001/0001830 A1 | 5/2001 | Dobak, III, et al. |
| 2001/0001831 A1 | 5/2001 | Dobak, III, et al. |
| 2001/0001832 A1 | 5/2001 | Dobak, III, et al. |
| 2001/0002442 A1 | 5/2001 | Dobak, III |
| 2001/0005791 A1 | 6/2001 | Ginsburg et al. |
| 2001/0007951 A1 | 7/2001 | Dobak, III |
| 2001/0008975 A1 | 7/2001 | Dobak, III, et al. |
| 2001/0010011 A1 | 7/2001 | Aliberto et al. |
| 2001/0011184 A1 | 8/2001 | Dobak, III, et al. |
| 2001/0011185 A1 | 8/2001 | Dobak, III, et al. |
| 2001/0016763 A1 | 8/2001 | Lasheras, et al. |
| 2001/0016764 A1 | 8/2001 | Dobak, III |
| 2001/0021865 A1 | 9/2001 | Dobak, III, et al. |
| 2001/0021866 A1 | 9/2001 | Dobak, III, et al. |
| 2001/0027333 A1 | 10/2001 | Schwartz |
| 2001/0029394 A1 | 10/2001 | Dobak, III, et al. |
| 2001/0031946 A1 | 10/2001 | Walker et al. |
| 2001/0032003 A1 | 10/2001 | Pecor |
| 2001/0032004 A1 | 10/2001 | Werneth |
| 2001/0039440 A1 | 11/2001 | Lasheras, et al. |
| 2001/0041923 A1 | 11/2001 | Dobak, III |
| 2001/0044644 A1 | 11/2001 | Keller, et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg, et al. |
| 2001/0049545 A1 | 12/2001 | Lasersohn et al. |
| 2002/0002394 A1 | 1/2002 | Dobak, III |
| 2002/0004675 A1 | 1/2002 | Lasheras |
| 2002/0007179 A1 | 1/2002 | Dobak, III, et al. |
| 2002/0007202 A1 | 1/2002 | Dobak, III, et al. |
| 2002/0007203 A1 | 1/2002 | Gilmartin, et al. |
| 2002/0016621 A1 | 2/2002 | Yon et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032474 A1 | 3/2002 | Dobak, III |
| 2002/0040717 A1 | 4/2002 | Dobak, III |
| 2002/0045892 A1 | 4/2002 | Kramer |
| 2002/0045925 A1 | 4/2002 | Keller, et al. |
| 2002/0049409 A1 | 4/2002 | Noda et al. |
| 2002/0049410 A1 | 4/2002 | Noda et al. |
| 2002/0049484 A1 | 4/2002 | Yon, et al. |
| 2002/0066458 A1 | 6/2002 | Aliberto et al. |
| 2002/0068964 A1 | 6/2002 | Dobak, III |
| 2002/0091378 A1 | 7/2002 | Dobak, III, et al. |
| 2002/0091429 A1 | 7/2002 | Dobak, III, et al. |
| 2002/0091430 A1 | 7/2002 | Dobak, III, et. al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103519 A1 | 8/2002 | Dobak, III, et al. |
| 2002/0111584 A1 | 8/2002 | Walker, et al. |
| 2002/0111616 A1 | 8/2002 | Dae, et al. |
| 2002/0111657 A1 | 8/2002 | Dae, et al. |
| 2002/0116041 A1 | 8/2002 | Daoud |
| 2002/0120314 A1 | 8/2002 | Evans, et al. |
| 2002/0128698 A1 | 9/2002 | Dobak, III |
| 2002/0138122 A1 | 9/2002 | Worthen et al. |

FOREIGN PATENT DOCUMENTS

| | | |
|---|---|---|
| WO | WO00/38601 A1 | 7/2000 |
| WO | WO00/47145 A1 | 8/2000 |
| WO | WO00/48670 A1 | 8/2000 |
| WO | WO00/51534 A1 | 9/2000 |
| WO | WO00/53135 A1 | 9/2000 |
| WO | WO00/57823 A1 | 10/2000 |
| WO | WO00/62837 A1 | 10/2000 |
| WO | WO00/06053 A1 | 11/2000 |
| WO | WO00/72779 A2 | 12/2000 |
| WO | WO00/72787 A1 | 12/2000 |
| WO | W0 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13809 | 3/2001 |
| WO | WO 01/13837 | 3/2001 |
| WO | WO 01/13984 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/56517 | 8/2001 |
| WO | WO 01/58397 | 8/2001 |
| WO | WO 01/60441 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 02/07793 | 1/2002 |
| WO | WO 02/26175 | 4/2002 |
| WO | WO 02/26176 | 4/2002 |
| WO | WO 02/26285 | 4/2002 |
| WO | WO 02/26307 | 4/2002 |
| WO | WO 02/28300 | 4/2002 |
| WO | WO 02/36180 | 5/2002 |
| WO | WO 02/38091 | 5/2002 |
| WO | WO 02/43577 | 6/2002 |
| WO | WO 02/055129 | 7/2002 |

\* cited by examiner

MULTIPURPOSE CATHETER ASSEMBLY

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The current invention relates to cooling or warming of the body of a patient, or selective cooling or warming of a selected organ, by cooling or warming the blood in a major artery, or cooling or warming the blood flowing into the selected organ. This thermal treatment can protect the tissue from injury caused by anoxia or trauma, or it can achieve other purposes.

2. Background Information

Organs of the human body, such as the brain, kidney, and heart, are maintained at a constant temperature of approximately 37° C. Cooling of organs below 35° C. is known to provide cellular protection from anoxic damage caused by a disruption of blood supply, or by trauma. Cooling can also reduce swelling associated with these injuries.

Hypothermia is currently utilized in medicine and is sometimes performed to protect the brain from injury. Cooling of the brain is generally accomplished through whole body cooling to create a condition of total body hypothermia in the range of 20° to 30° C. This cooling is accomplished by immersing the patient in ice, by using cooling blankets, or by cooling the blood flowing externally through a cardiopulmonary bypass machine.

Some physicians have immersed the patient's head in ice to provide brain cooling. There are also cooling helmets, or head gear, to perform the same. This approach suffers from the problems of slow cool down and poor temperature control due to the temperature gradient that must be established externally to internally. It has also been shown that complications sometimes associated with total body cooling, such as arrhythmia and decreased cardiac output, can also be caused by cooling of the face and head only.

Selective organ hypothermia has also been attempted by perfusing the organ with a cold solution, such as saline or perflourocarbons. This is commonly done to protect the heart during heart surgery and is referred to as cardioplegia. This procedure has a number of drawbacks, including limited time of administration due to excessive volume accumulation, cost and inconvenience of maintaining the perfusate, and lack of effectiveness due to temperature dilution from the blood. Temperature dilution by the blood is a particular problem in high blood flow organs such as the brain. For cardioplegia, the blood flow to the heart is minimized, and therefore this effect is minimized.

Intravascular hypothermia, created by cooling the blood flowing in a selected artery, avoids many of the aforementioned complications. First, because the blood is cooled intravascularly, or in situ, problems associated with external circulation of blood are eliminated. Second, only a single puncture and arterial vessel cannulation is required, and it can be performed at an easily accessible artery such as the femoral, subclavian, or brachial. Third, cold perfilsate solutions are not required, thus eliminating problems with excessive fluid accumulation. This also eliminates the time, cost, and handling issues associated with providing and maintaining cold perfusate solution. Fourth, rapid cooling can be achieved. Fifth, precise temperature control is possible.

One important factor related to catheter development for hypothermia is the small size of the artery in which the catheter may be placed, and the need to prevent a significant reduction in blood flow when the catheter is placed in the artery. A significant reduction in blood flow would result in ischemic organ damage. This situation is exacerbated if, for instance, cooling of the blood in an artery results in the constriction of the artery in the area where cooling is applied.

BRIEF SUMMARY OF THE INVENTION

The cooling achieved by the present invention is accomplished by placing a substantially coaxial cooling catheter into the feeding artery of the selected organ, or into a major artery. Cold saline solution is circulated through the catheter. In the catheter, a fluid supply lumen would carry the saline solution to a distal heat transfer element where cooling would occur. A preferred heat transfer element would be flexible and axially compressible. Cooling of the catheter tip to the desired temperature results in cooling of the blood flowing in the artery.

It is important for the catheter to be flexible in order to successfully navigate the arterial path, and this is especially true of the distal end of the catheter. So, the distal end of the catheter should have a flexible heat transfer element, which is composed of a material which conducts heat better than the remainder of the catheter. The catheter body material could be nylon or PBAX, and the heat transfer element could be made from a material having higher thermal conductivity, such as nitinol, nickel, copper, silver, or gold. Ideally, the heat transfer element is formed with a maximized or convoluted surface area, which can for example include a bellows or helically shaped ridges and grooves.

To counteract any tendency of the artery to constrict upon cooling, an exit port is formed in the catheter, to allow a very small flow of the cooling saline solution to exit the catheter in the proximity of the heat transfer element. A vaso-dilator, such as papaverine, is mixed with the saline solution, resulting in a dual purpose treatment fluid. The papaverine in the saline solution acts upon the artery to prevent it from constricting. Alternatively, the medicament, such as a vaso-dilator, can be delivered to the exit port via a separate lumen, rather than being mixed with the saline solution.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
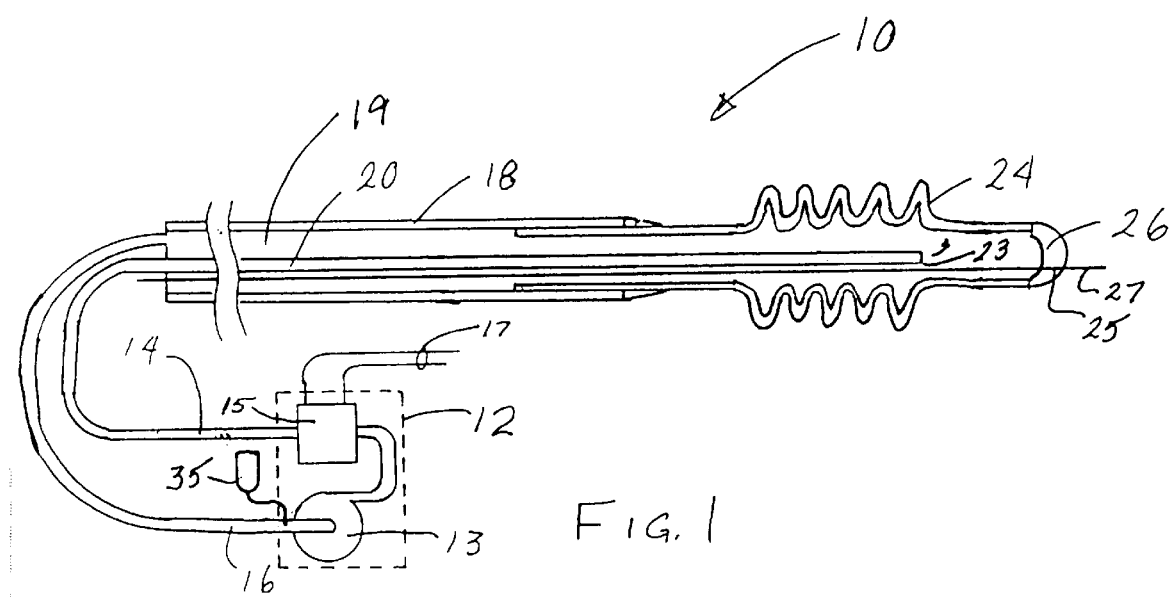
FIG. 1 is a schematic view of a first embodiment of the present invention, with a treatment fluid duct and a guidewire penetration.

As shown in FIG. 1, the apparatus of the present invention includes a flexible substantially coaxial catheter assembly 10, fed by a saline pumping or circulating unit 12, which can include a pump 13 and a chiller 15, with a freon based refrigerant loop 17. The circulating unit 12 has an outlet 14 and an inlet 16. Introduction of a medicament, such as a vaso-dilator, into the saline solution can be accomplished at the circulating unit 12. This can be done by means of any of several known fluid metering devices. For example, a reservoir 35 of the medicament can feed the inlet 16 of the pump 13. Alternatively, the medicament could be introduced at other locations along the catheter assembly 10.

The catheter assembly 10 has a flexible outer catheter 18. The catheter assembly also has a flexible inner supply catheter 20 for delivery of the treatment fluid, which consists of the saline solution and the vaso-dilator. The inner supply catheter 20 is insertable into the outer catheter 18. The catheter assembly 10 can be made of nylon, polyimide, PBAX, or other suitable catheter material. Both the outer catheter 18 and the supply catheter 20 could be insulated.

The lumen of the supply catheter 20 serves as the supply flow path for the circulating treatment fluid, while the lumen 19 of the outer catheter 18 serves as the return flow path for the circulating treatment fluid. The outer catheter 18 and the supply catheter 20 must be flexible, to enable passage through the vascular system of the patient to the selected artery. The length and diameter of the outer catheter 18 and supply catheter 20 are designed for the size and location of the artery in which the apparatus will be used. For use in the internal carotid artery to achieve hypothermia of the brain, the outer catheter 18 and the supply catheter 20 will have a length of approximately 70 to 100 centimeters.

Figure 2:
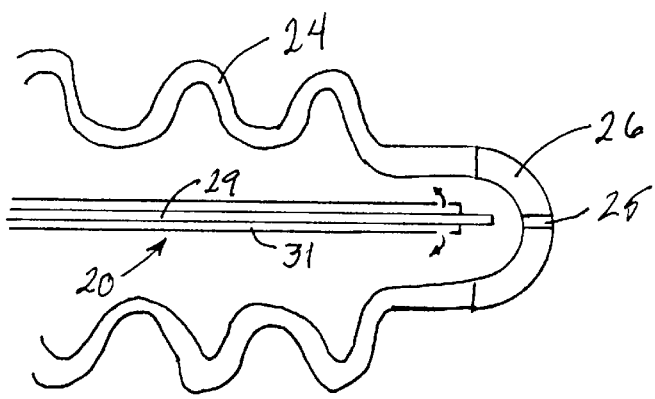
FIG. 2 is a partial longitudinal section view of the distal end of a second embodiment of the present invention, showing a treatment fluid catheter assembly and a medicament valve.
Figure 3:
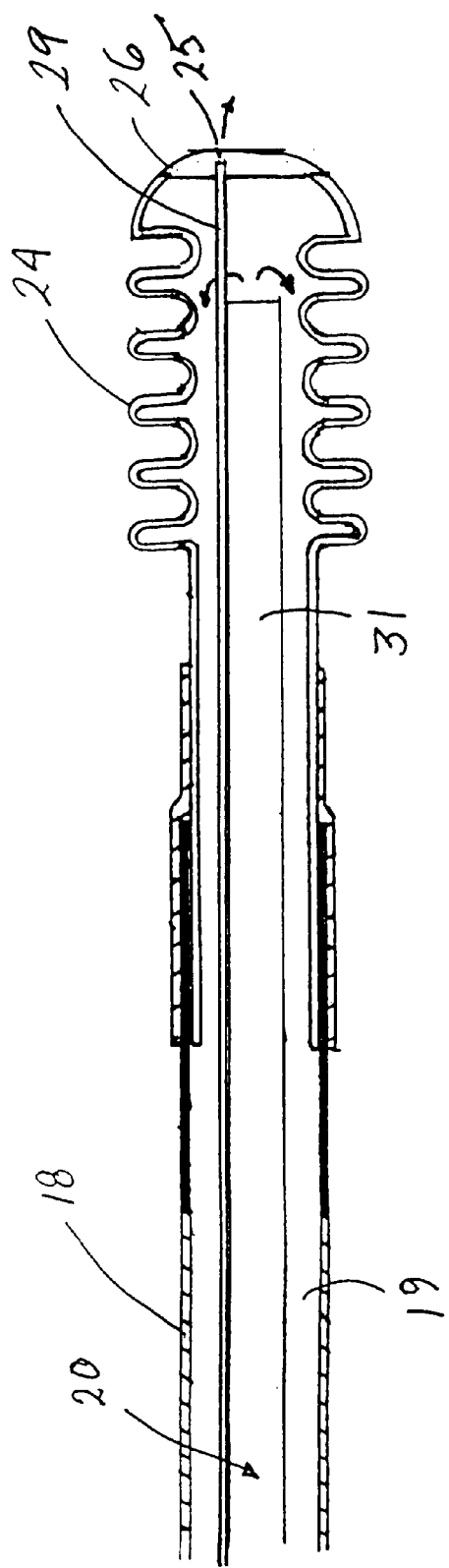
FIG. 3 is a partial longitudinal section view of a third embodiment of the present invention, showing a medicament duct leading to a rupturable membrane at the distal end of the heat transfer element.

The circulating unit outlet 14 is attached in fluid flow communication, by known means, to a proximal end of the supply catheter 20 disposed coaxially within the outer catheter 18. The distal end of the supply catheter 20 has an outlet which is positioned adjacent to or within a chamber of a flexible heat transfer element 24. The heat transfer element can be flexible, to enable passage through the vascular system of the patient to the selected artery. As shown in FIGS. 1, 2, and 3, the heat transfer element 24 can be a bellows, or it can have a helical surface contour, or it can be a combination of alternating helices and bellows. One or more radiographic markers, as is known in the art, can be incorporated into the heat transfer element 24, or an end cap 26, or another nearby portion of the catheter assembly 10.

A dual purpose treatment fluid, consisting of saline solution and a vaso-dilator, is chilled and pumped through the supply catheter 20, exiting the supply catheter 20 via one or more supply ports 23 into the interior chamber of the heat transfer element 24, thereby cooling the heat transfer element 24. Blood in the artery flows around the heat transfer element 24, thereby being cooled. The blood then continues to flow through the artery, cooling the body or the selected organ. A very small exit port 25 can be formed in a pliable end cap 26 by threading of a guide wire 27 through the end cap 26. The end cap 26 can be formed of a pliable material such as a soft polymer or silicone sealant. Insertion of the guide wire 27 can also facilitate insertion of the catheter assembly 10 into the blood vessel. When the guide wire 27 is removed from the catheter assembly 10, the resealable exit port 25 is left in the end cap 26. A minute flow of the treatment fluid is allowed to exit the outer catheter 18 via the exit port 25 when the saline pressure is increased. The vast majority of the treatment fluid then flows back to the circulating unit 12 via the return lumen 19 of the outer catheter 18.

As shown in FIG. 2, the inner supply catheter 20 can incorporate an elongate member 29 in addition to the treatment fluid supply lumen 31. If used in the embodiment shown in FIG. 1, this dual member supply catheter could have a temperature control lumen 31 for supplying the temperature controlled fluid and a separate lumen in the elongate member 29 for delivery of the medicament. Alternatively, as shown in FIG. 2, the elongate member 29 could be a solid member, the distal end of which is used to selectively plug and unplug a valve or slot 25 in the end cap 26, to selectively allow medicament to escape the outer catheter 18 mixed with the saline solution as a dual purpose treatment fluid. As still another alternative, the elongate member 29 could comprise a medicament delivery duct which contains a separate medicament delivery lumen for delivering medicament in the embodiment shown in FIG. 2. In this last example, the distal end of the medicament delivery duct 29 could be forced through the valve or slot 25 in the end cap 26, followed by delivery of the medicament through the medicament delivery lumen. Withdrawal of the medicament delivery duct 29 from the valve 25 would allow the valve 25 to reseal, preventing the escape of saline solution.

As shown in FIG. 3, an elongate medicament delivery duct 29 can terminate within the pliable end cap 26, with a thin layer of end cap material covering the distal end of the medicament delivery duct 29. Pressurization of the medicament delivery duct 29 can rupture this thin layer of end cap material, thereby forming a resealable exit port 25, and allowing medicament to exit the outer catheter 18 through the exit port 25. Formation of the exit port 25 in this manner can be facilitated by forming a weak spot or stress riser, such as a partial depth cut, in the end cap 26 at the distal end of the medicament delivery duct 29. Depressurization of the medicament delivery duct 29 would allow the rupture in the thin layer of end cap material to close, preventing escape of saline solution from the temperature control lumen 31.

Figure 4:
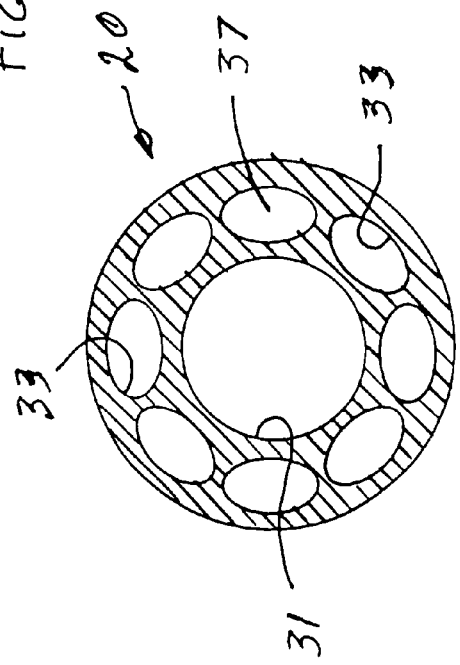
FIG. 4 is a transverse section of one embodiment of a multilumen catheter which may be used in the present invention to deliver temperature controlled fluid and medicament.

FIG. 4 illustrates another way in which a supply catheter assembly 20 can separately deliver temperature controlled fluid and medicament to the heat transfer element 24, for use in the embodiments discussed above. One lumen 31 of the multilumen catheter assembly 20 can be used to supply temperature controlled fluid, while other lumens 33 can be used to supply one or more medicaments, and still another lumen 37 can serve as a guide wire lumen. If desired, several of the lumens can be evacuated or filled with insulating material, rather than being used as supply lumens, to insulate the supply catheter assembly 20.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. An apparatus for delivery of thermal treatment and medication to a selected area in the vascular system of a patient, comprising:

an elongated flexible catheter assembly;

a heat transfer element on a distal portion of said catheter assembly insertable to said selected area in said vascular system;

a supply duct in said catheter assembly, said supply duct being in fluid flow communication with said heat transfer element, to supply a treatment fluid to said heat transfer element;

a return lumen in said catheter assembly, said return lumen being in fluid flow communication with said heat transfer element, to receive said treatment fluid from said heat transfer element; and an exit port in fluid flow communication with said supply duct to allow a portion of said treatment fluid to exit said catheter assembly in the proximity of said heat transfer element.

2. The apparatus recited in claim 1, wherein said exit port is adapted to open upon pressurization of said supply duct and close upon de-pressurization of said supply duct.

3. The apparatus recited in claim 2, wherein said exit port comprises a resealable hole formed by passing a guide wire through a distal portion of said apparatus.

4. The apparatus recited in claim 2, wherein said exit port comprises a rupturable and resealable closure at a distal portion of said apparatus.

5. The apparatus recited in claim 2, wherein said exit port comprises a selectively operable valve formed at a distal portion of said apparatus.

6. The apparatus recited in claim 5, wherein said valve is operated by insertion and removal of said supply duct.

7. The apparatus recited in claim 1, further comprising a treatment fluid supply source adapted to deliver a medicament mixed with a temperature controlled fluid to said supply duct.

8. The apparatus recited in claim 7, wherein said medicament comprises a vaso-dilator.

9. The apparatus recited in claim 1, further comprising:

first and second supply lumens; and a treatment fluid supply source adapted to deliver a temperature controlled fluid to said first supply lumen, said treatment fluid supply source being adapted to deliver a medicament to said second supply lumen.

10. The apparatus recited in claim 9, wherein said medicament comprises a vaso-dilator.

11. An apparatus as recited in claim 1, wherein said catheter assembly comprises:

an outer catheter defining said return lumen, said heat transfer element comprising a distal portion of said outer catheter; and a supply catheter defining at least a portion of said supply duct, said supply catheter being insertable into said outer catheter;

wherein said exit port is located in a distal portion of said outer catheter, to allow exit of a portion of said treatment fluid from said outer catheter.

12. An apparatus as recited in claim 11, further comprising:

a valve in said distal portion of said outer catheter, said exit port being located in said valve; and a distal end on said supply catheter configured to actuate said valve to allow a portion of said treatment fluid to exit said outer catheter via said valve.

13. An apparatus as recited in claim 11, further comprising a guide lumen in said supply catheter for passage of an elongated member through said supply catheter.

14. An apparatus as recited in claim 13, wherein said elongated member is a guide wire.

15. An apparatus for delivery of thermal treatment and medication to a selected area in the vascular system of a patient, comprising:

an elongated flexible catheter assembly;

a heat transfer element on a distal portion of said catheter assembly insertable to said selected area in said vascular system;

a temperature control lumen within said catheter assembly, said temperature control lumen being in fluid flow communication with said heat transfer element, to supply a temperature controlled fluid to said heat transfer element;

a medicament delivery lumen within said catheter assembly, said medicament delivery lumen being in fluid flow communication with said distal portion of said catheter assembly, to deliver a medicament to said distal portion of said catheter assembly;

a return lumen in said catheter assembly, said return lumen being in fluid flow communication with said heat transfer element, to receive said temperature controlled fluid from said heat transfer element; and an exit port in said distal portion of said catheter assembly, said exit port being in fluid flow communication with said medicament delivery lumen to allow said medicament to exit said catheter assembly in the proximity of said heat transfer element.

16. The apparatus recited in claim 15, wherein said exit port is adapted to open upon pressurization of said medicament delivery lumen and close upon de-pressurization of said medicament delivery lumen.

17. The apparatus recited in claim 16, wherein said exit port comprises a resealable hole formed by passing a guide wire through a distal portion of said catheter assembly.

18. The apparatus recited in claim 16, wherein said exit port comprises a rupturable and resealable closure at a distal portion of said catheter assembly.

19. The apparatus recited in claim 16, wherein said exit port comprises a selectively operable valve formed at a distal portion of said catheter assembly.

20. The apparatus recited in claim 19, wherein said valve is operated by insertion and removal of said medicament delivery lumen.

21. The apparatus recited in claim 15, further comprising a supply source adapted to deliver said temperature controlled fluid to said temperature control lumen, said supply source being adapted to deliver said medicament to said medicament delivery lumen.

22. The apparatus recited in claim 21, wherein said medicament comprises a vaso-dilator.

23. An apparatus as recited in claim 15, wherein said catheter assembly comprises:

an outer catheter defining said return lumen, said heat transfer element comprising a distal portion of said outer catheter; and a supply catheter defining at least a portion of said temperature control lumen and at least a portion of said medicament delivery lumen, said supply catheter being insertable into said outer catheter;

wherein said exit port is located in a distal portion of said outer catheter, to allow exit of said medicament from said outer catheter.

24. An apparatus as recited in claim 23, further comprising:

a valve in said distal portion of said outer catheter, said exit port being located in said valve; and a distal end on said supply catheter configured to actuate said valve to allow said medicament to exit said outer catheter via said valve.

* * * * *